US008407234B1

(12) United States Patent
Buschbach

(10) Patent No.: US 8,407,234 B1
(45) Date of Patent: Mar. 26, 2013

(54) ORDERING A LIST EMBODYING MULTIPLE CRITERIA

(75) Inventor: Thomas Justin Buschbach, Kenner, LA (US)

(73) Assignee: inFRONT Devices & Systems LLC, Mandeville, LA (US)

( * ) Notice: Subject to any disclaimer, the term of this patent is extended or adjusted under 35 U.S.C. 154(b) by 171 days.

(21) Appl. No.: 12/758,074

(22) Filed: Apr. 12, 2010

Related U.S. Application Data

(60) Provisional application No. 61/202,841, filed on Apr. 10, 2009.

(51) Int. Cl.
*G06F 17/30* (2006.01)
(52) U.S. Cl. ........................................ 707/752
(58) Field of Classification Search ............... 707/752
See application file for complete search history.

(56) References Cited

U.S. PATENT DOCUMENTS

| | | | |
|---|---|---|---|
| 5,321,833 A | 6/1994 | Chang et al. | |
| 5,706,449 A | 1/1998 | Liu et al. | |
| 5,774,121 A | 6/1998 | Stiegler | |
| 5,826,260 A | 10/1998 | Byrd et al. | |
| 7,028,027 B1 | 4/2006 | Zha et al. | |
| 7,587,391 B1 | 9/2009 | Bostock et al. | |
| 7,603,362 B2 | 10/2009 | Elliott et al. | |
| 2002/0165814 A1* | 11/2002 | Lee et al. | 705/37 |
| 2004/0153389 A1 | 8/2004 | Lortscher | |
| 2004/0267762 A1* | 12/2004 | Tunning et al. | 707/100 |
| 2006/0212449 A1* | 9/2006 | Novy | 707/7 |
| 2007/0011153 A1 | 1/2007 | Pillai et al. | |
| 2007/0271296 A1* | 11/2007 | Purang et al. | 707/104.1 |
| 2009/0157720 A1* | 6/2009 | Kolcz et al. | 707/102 |

OTHER PUBLICATIONS

Isikman, Omer O. et al., "Adaptive Weighted Multi-Criteria Fuzzy Query Processing for Web Based Real Estate Applications", Symposium on Applied Computing, Processing of the 20058 ACM Symposium, 2008, pp. 987-991.
Meyer, Patrick et al., "Choice, Ranking and Sorting in Fuzzy Multiple Criteria Decision Aid", Multiple Criteria Decision Analysis, Chapter 12, Department of Mathematics, 2005, pp. 471-506.

* cited by examiner

*Primary Examiner* — Rehana Perveen
*Assistant Examiner* — Alexander Khong
(74) *Attorney, Agent, or Firm* — Robert Plotkin, P.C.

(57) ABSTRACT

A computer-automated system orders a list of elements according to multiple criteria. Each element in a data set may have any number of attributes. Attributes may have corresponding weights which differ from each other. The system orders the elements based on the weight of the attributes and the attributes associated the elements. In particular, the system may combine the weights of all attributes associated with a particular element to produce a combined weight for the element. The system may tend to place elements having relatively high combined weights closer to the beginning of the list than elements having relatively low combined weights. The system may be used in a variety of applications, such as coordinating the schedules of multiple workers in a hospital or other workplace, based on multiple needs of the workplace and multiple preferences of the workers.

12 Claims, 14 Drawing Sheets

ORDERING A LIST EMBODYING MULTIPLE CRITERIA

CROSS REFERENCE TO RELATED APPLICATIONS

This application claims priority from U.S. Provisional Patent Application Ser. No. 61/202,841, filed on Apr. 10, 2009, entitled "Method for Ordering a List Embodying Multiple Criteria," which is hereby incorporated by reference.

BACKGROUND

Coordinating the schedules of multiple people is a difficult problem. For example, in any workplace it is necessary to coordinate employees' schedules so that the workplace is fully staffed at all times, even as the availability of individual employees changes due to illness, vacations, changes in personnel, and other causes. Scheduling problems are particularly difficult in facilities such as hospitals, which have a large number of employees serving in a wide variety of roles, where both demand and availability vary frequently, and where the need to avoid gaps in coverage is particularly significant. Coordinating employee schedules in such an environment in a way that satisfies the staffing needs of the hospital while satisfying the personal needs of the employees can be particularly challenging.

For these and other reasons, computers have long been used in an attempt to facilitate scheduling. At first, computer-based scheduling systems were used in an attempt to perform what was referred to as "optimizing the workforce," in an effort to match labor supply with demand as closely as possible in the face of frequent shifts in both supply (e.g., a nurse calling in sick) and demand (e.g., an emergency surgery patient entering the hospital). Most automated scheduling software continues to be focused on such optimization.

So-called workforce optimization, however, leaves much to be desired. For example, scheduling is one of the only processes that must be revisited by many people within a large organization, such as a hospital, many times within a week, as both supply and demand fluctuate. Nurses, for example, must use the scheduling system to check their schedules and request time off. Management must use the scheduling system to view schedule change requests and to update schedules within the system. As a result, an automated scheduling system should be capable of responding to frequently-changing inputs from multiple users both quickly. Existing workforce optimization software, however, typically responds to such changes slowly, unless large and expensive computing equipment is employed.

Some studies estimate that the U.S. healthcare system will fall short by 800,000-1 million nurses by the year 2020. Therefore it would be highly desirable to take steps to retain existing nurses. Yet there is a lack of any existing computer-based tools for retaining nurses. The most important factor in retaining nurses is providing them with a work schedule that matches their needs, including having time off for their outside lives. If their schedules do not match their needs, they will leave for another job. Therefore, there is a great need for a scheduling system that could more accurately match the needs of individual nurses with their work schedules. The same is true more generally for all employees and other workers.

SUMMARY

A computer-automated system orders a list of elements according to multiple criteria. Each element in a data set may have any number of attributes. Attributes may have corresponding weights which differ from each other. The system orders the elements based on the weight of the attributes and the attributes associated the elements. In particular, the system may combine the weights of all attributes associated with a particular element to produce a combined weight for the element. The system may tend to place elements having relatively high combined weights closer to the beginning of the list than elements having relatively low combined weights. The system may be used in a variety of applications, such as coordinating the schedules of multiple workers in a hospital or other workplace, based on multiple needs of the workplace and multiple preferences of the workers.

For example, one embodiment of the present invention is directed to a computer-implemented method for ordering a plurality of elements, wherein each of the plurality of elements has at least one corresponding attribute. The method includes: (A) identifying a first subset of the plurality of elements associated with a first attribute by selecting, from among the plurality of elements, at least one element having the first attribute; (B) identifying a first weight associated with the first attribute; (C) removing, from the first subset, a number of elements based on the first weight, to produce a first reduced subset of the plurality of elements; (D) identifying a second subset of the plurality of elements associated with a second attribute by selecting, from among the plurality of elements, at least one element having the second attribute; (E) identifying a second weight associated with the second attribute, wherein the second weight differs from the first weight; (F) removing, from the second subset, a number of elements based on the second weight, to produce a second reduced subset of the plurality of elements; and (G) identifying a plurality of regions, each of which corresponds to a distinct combination of zero or more of the first and second attributes.

Another embodiment of the present invention is directed to a computer-implemented method for ordering a plurality of elements, wherein each of the plurality of elements has at least one corresponding attribute. The method includes: (A) identifying a first subset of the plurality of elements associated with a first attribute by selecting, from among the plurality of elements, at least one element having the first attribute; (B) identifying a first weight associated with the first attribute; (C) identifying a second subset of the plurality of elements associated with a second attribute by selecting, from among the plurality of elements, at least one element having the second attribute; (D) identifying a second weight associated with the second attribute, wherein the second weight differs from the first weight; (E) identifying a plurality of regions, each of which corresponds to a distinct combination of zero or more of the first and second attributes; and (F) for each region R in the plurality of regions, identifying a corresponding weight sum for region R comprising a sum of the weights of the zero or more attributes corresponding to R.

Other features and advantages of various aspects and embodiments of the present invention will become apparent from the following description and from the claims.

DETAILED DESCRIPTION

A computer-automated system orders a list of elements according to multiple criteria. Each element in a data set may have any number of attributes. Attributes may have corresponding weights which differ from each other. The system orders the elements based on the weight of the attributes and the attributes associated the elements. In particular, the system may combine the weights of all attributes associated with a particular element to produce a combined weight for the element. The system may tend to place elements having relatively high combined weights closer to the beginning of the list than elements having relatively low combined weights. The system may be used in a variety of applications, such as coordinating the schedules of multiple workers in a hospital or other workplace, based on multiple needs of the workplace and multiple preferences of the workers.

Figure 1A:
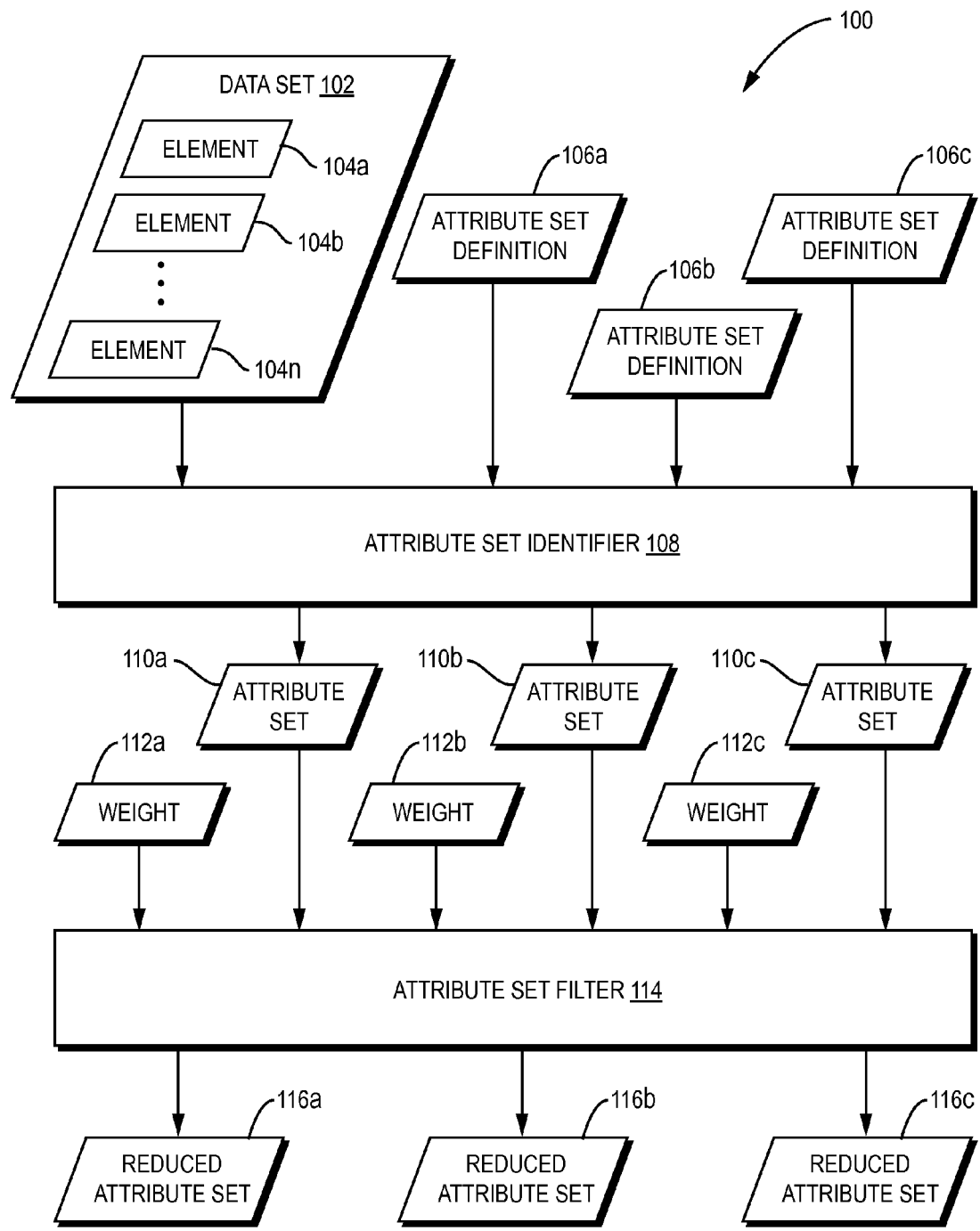
FIG. 1A is a dataflow diagram of a system for ordering a list embodying multiple criteria according to one embodiment of the present invention.
Figure 2A:
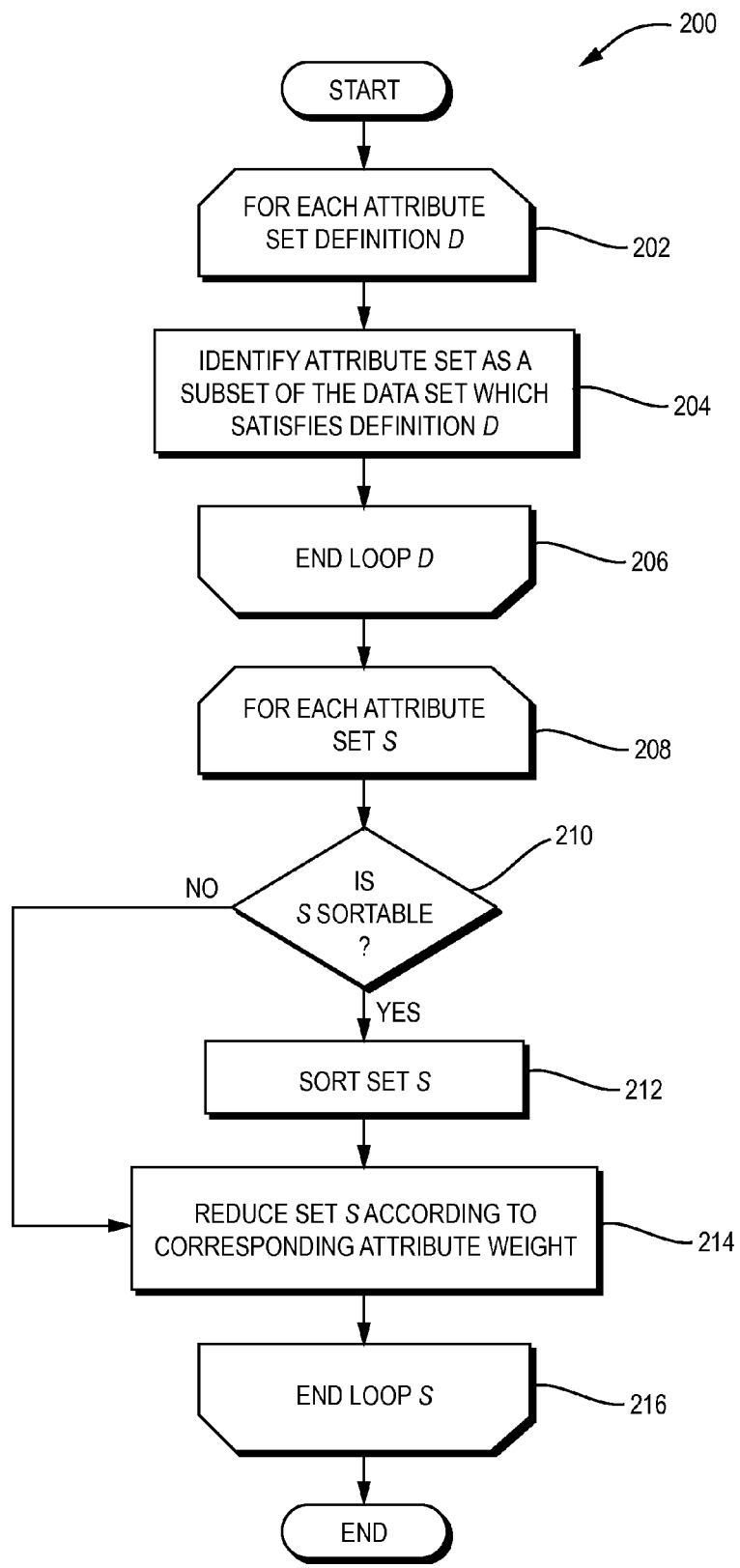
FIG. 2A is a flowchart of a method performed by the systems of FIGS. 1A and 1B according to one embodiment of the present invention.

More specifically, referring to FIG. 1A, a dataflow diagram is shown of a system 100 for ordering a list embodying multiple criteria according to one embodiment of the present invention. Referring to FIG. 2A, a flowchart is shown of a method 200 performed by the system 100 of FIG. 1A according to one embodiment of the present invention.

Figure 3A:
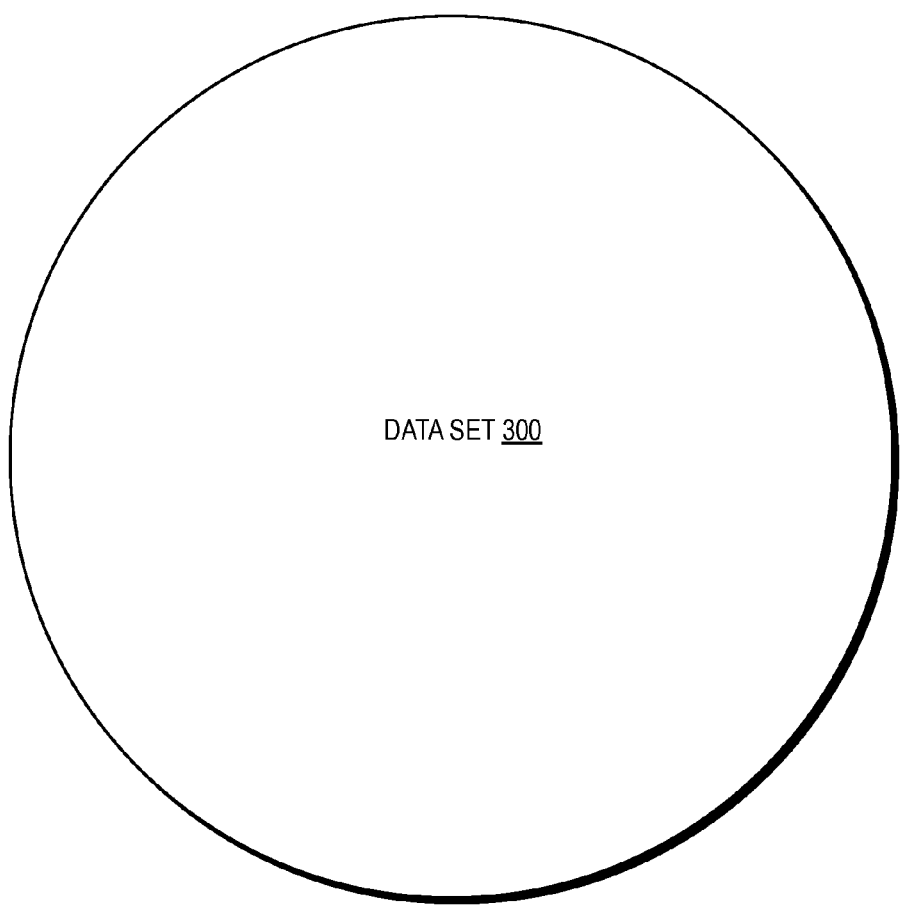
FIG. 3A is a diagram of a data set containing a plurality of attributes according to one embodiment of the present invention.

The system 100 of FIG. 1A includes a data set 102, which includes a plurality of elements 104a-n, where n may be any number. Although only a few elements are shown in FIG. 1A for ease of illustration, in practice there may be hundreds, thousands, or more elements in the data set 102. The term "element" as used herein refers to any unit of data, regardless of the kind of data, and regardless of the logical and/or physical format in which the data are stored. For example, an element may be a record or field in a database, but this is merely an example and not a requirement of the present invention. Similarly, the data set 102 may be any collection of elements, regardless of the logical and/or physical format in which the data set 102 is stored. For example, the data set 102 may be a database, but this is merely an example and not a requirement of the present invention. Referring to FIG. 3A, an example of the data set 102 is illustrated as a circle 300, in which the filled interior of the circle graphically represents all of the elements 104a-n in the data set 102.

Each of the elements 104a-n may have zero or more attributes. As used herein the term "attribute" refers to any quality or characteristic possesed by an element which allows the element to be grouped together with other elements possessing the same or similar qualities or characteristics. For example, if each of the elements 104a-n represents a distinct worker at a hospital, then some of the elements 104a-n may have an "employee" attribute indicating that the corresponding worker is an employee of the hospital (rather than, for example, an independent contractor). Such an attribute may be represented within the elements 104a-n in any of a variety of ways. For example, if element 104a represents an employee, then element 104a may contain an "employee" field which is lacking in elements which do not represent employees. As another example, all elements 104a-n may contain the employee field, but elements (such as element 104a) representing employees may contain a first value for the employee field (e.g., "true"), while elements not representing employees may contain a second value for the employee field (e.g., "false"). These are merely examples of ways in which attributes may be represented within elements, which do not constitute limitations of the present invention.

As the "employee" attribute example illustrates, some attributes may represent binary characteristics, such that any particular element either has or does not have the attribute. Attributes need not, however, be binary. Rather, an attribute may have a plurality of (discrete or continuous) possible values. For example, some or all of the elements 104a-n may have a "work on weekends" attribute which represents the preference of the corresponding worker for working on weekends. Such an attribute may, for example, have a range of integer values ranging from 1 (strongly prefer not to work on weekends) through 10 (strongly prefer to work on weekends). Note that in this example, any number of the elements 104a-n may have such a "work on weekends" attribute, each with any value, and any number of elements 104a-n may lack such a "work on weekends" attribute entirely.

Attributes may be defined in more complex ways. For example, assume that some of the elements 104a-n have the "work on weekends" attribute with varying values. In this case, a "strongly prefer to work on weekends" attribute may be defined, such that elements which have the "work on weekends" attribute with a value higher than 7 are considered to have the (binary) "strongly prefer to work on weekends" attribute.

Elements 104a-n in the data set 102 may have any combination of attributes with any combination of values. As the examples below will make clear, any individual element may have any number of attributes (including zero), and multiple elements share one or more attributes in common. As another example, any particular attribute may be possessed by exactly one element in the data set 102.

Returning to FIG. 3A, recall that the data set 300 corresponds to the data set 102 in FIG. 1A, which includes a plurality of elements 104a-n. Because of this correspondence, in the discussion below, some references will be made to the data set 102, while other references may be made to the data set 300, for ease of explanation. Note, however, that any reference to the data set 102 (FIG. 1A) applies equally to the data set 300 (FIG. 3A) and vice versa.

Furthermore, note that the elements 104a-n may previously have been selected as a subset of a larger data set (not shown). For example, the elements 104a-n may have been pre-selected as the set of all elements from a larger data set which share specified attributes in common or which otherwise satisfy a particular query. The techniques disclosed herein, however, apply equally to the data set 102 regardless of how the elements 104a-n of the data set 102 were selected for inclusion in the data set 102.

For purposes of example, assume that the data set 300 contains one thousand elements (i.e., that n=1000 with respect to elements 104*a-n* in FIG. 1A). Further assume, for purposes of example, that certain attributes referred to herein simply as attributes A, B, and C are possessed by certain elements in the data set 300. As the discussion below will make clearer, this does not necessarily mean that all elements in the data set 300 have all of the attributes A, B, and C. Rather, each of the elements in the data set 300 may have any zero or more of the attributes A, B, and C. Furthermore, although three attributes are used in this particular example, the techniques disclosed herein may be applied equally to any number of attributes (e.g., 2, 3, 4, or more attributes).

The term "attribute set" refers herein to a set of elements that have a particular attribute or combination of attributes which define the attribute set. For example, an attribute set defined by possession of attribute A would contain all of those elements in the data set 300, and only those elements, which possess attribute A. Similarly, an attribute set defined by possession of attribute B would contain all of those elements in the data set 300, and only those elements, which possess attribute B. Since an element may contain both attributes A and B, a single element may be a member of both attribute set A and attribute set B. In other words, attribute sets A and B may overlap (intersect).

For ease of explanation, the following discussion will use the term "attribute set A" to refer to an attribute set defined solely by possession of attribute A, "attribute set B" to refer to an attribute set defined solely by possession of attribute B, and "attribute set C" to refer to an attribute set defined solely by possession of attribute C.

The system 100 of FIG. 1A and method 200 of FIG. 2A may identify attribute sets from the data set 102 as follows. The system 100 may include any number of attribute set definitions. For example, in FIG. 1A, three attribute set definitions 106*a-c* are shown for purposes of example. The attribute set definitions 106*a-c* may be created and provided to the system 100 in any of a variety of ways. For example, a user may create each of the attribute set definitions 106*a-c*. The techniques disclosed herein, however, may be used regardless of how the attribute set definitions 106*a-c* are created and provided to the system 100.

Each of the attribute set definitions 106*a-c* may define a corresponding attribute set in any of a variety of ways, such as by specifying one or more attributes. In the following discussion, it will be assumed for purposes of example that attribute set definition 106*a* defines an attribute set solely based on possession of attribute A, that attribute set definition 106*b* defines an attribute set solely based on possession of attribute B, and that attribute set definition 106*c* defines an attribute set solely based on possession of attribute C.

Figure 3B:
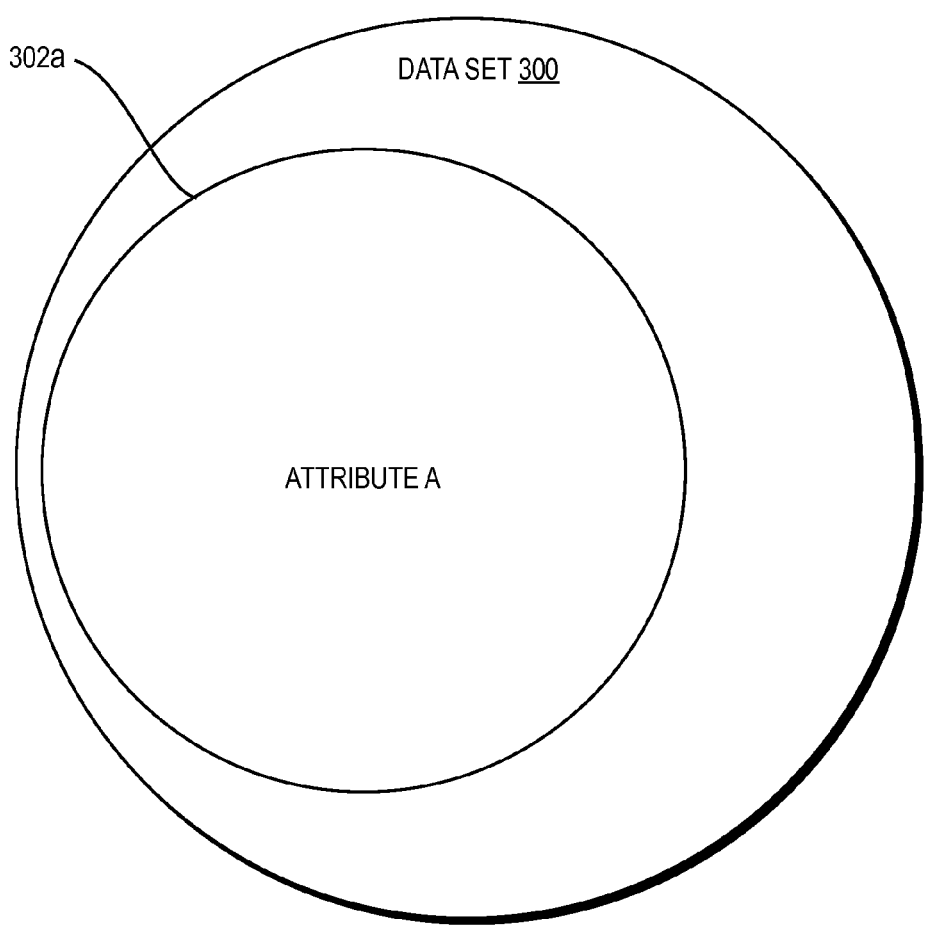
FIGS. 3B-3D are diagrams of attribute sets within the data set of FIG. 3A according to one embodiment of the present invention.

For each of the attribute set definitions 106*a-c* (FIG. 2A, step 202), an attribute set identifier 108 in the system 100 (FIG. 1A) identifies a corresponding attribute set as the subset of elements in the data set 102 which satisfies the attribute set definition (FIG. 2A, steps 204, 206). For example, the attribute set identifier 108 uses attribute set definition 106*a* to identify attribute set 110*a* as the subset of the data set 102 which possesses attribute A. A graphical illustration of attribute set 110*a* is shown in FIG. 3B as attribute set 302*a*. Assume for purposes of example that attribute set 302*a* contains those 500 elements of data set 300 which possess attribute A. The portion of data set 300 in FIG. 3B which is not within attribute set 302*a* are those 500 elements of data set 300 which do not possess attribute A.

Figure 3C:
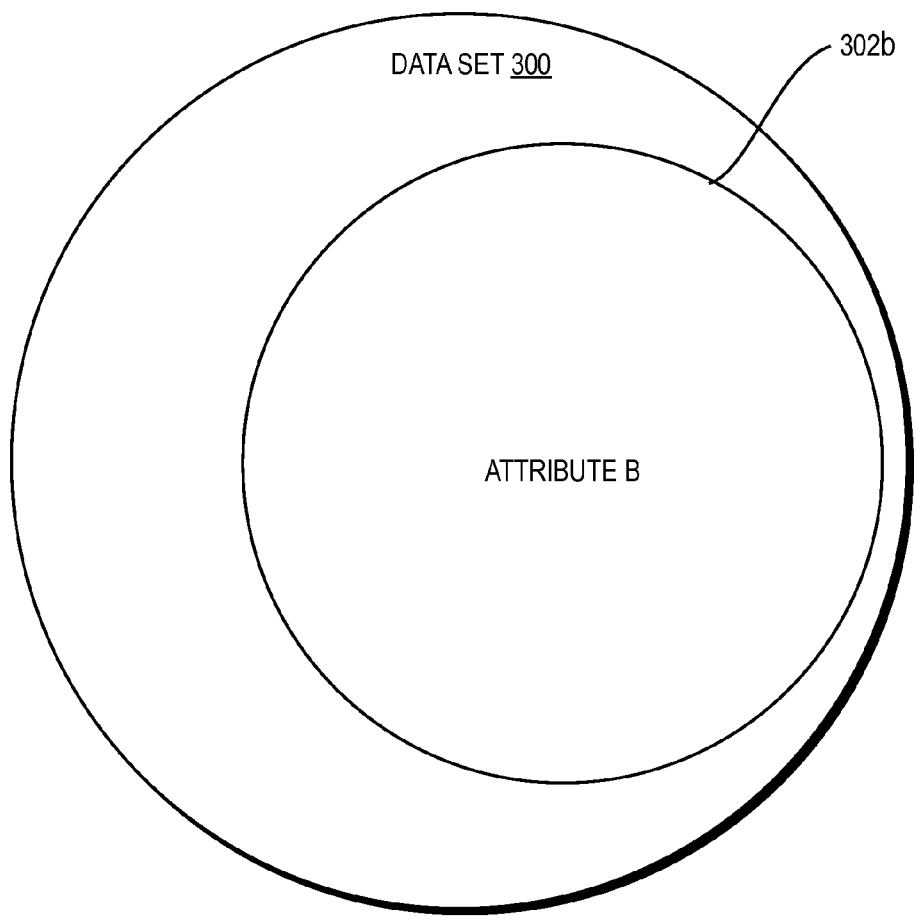

Similarly, the attribute set identifier 108 uses attribute set definition 106*b* to identify attribute set 110*b* as the subset of the data set 102 which possesses attribute B. A graphical illustration of attribute set 110*b* is shown in FIG. 3C as attribute set 302*b*. Assume for purposes of example that attribute set 302*b* contains those 500 elements of data set 300 which possess attribute B. The portion of data set 300 in FIG. 3C which is not within attribute set 302*b* are those 500 elements of data set 300 which do not possess attribute B.

Figure 3D:
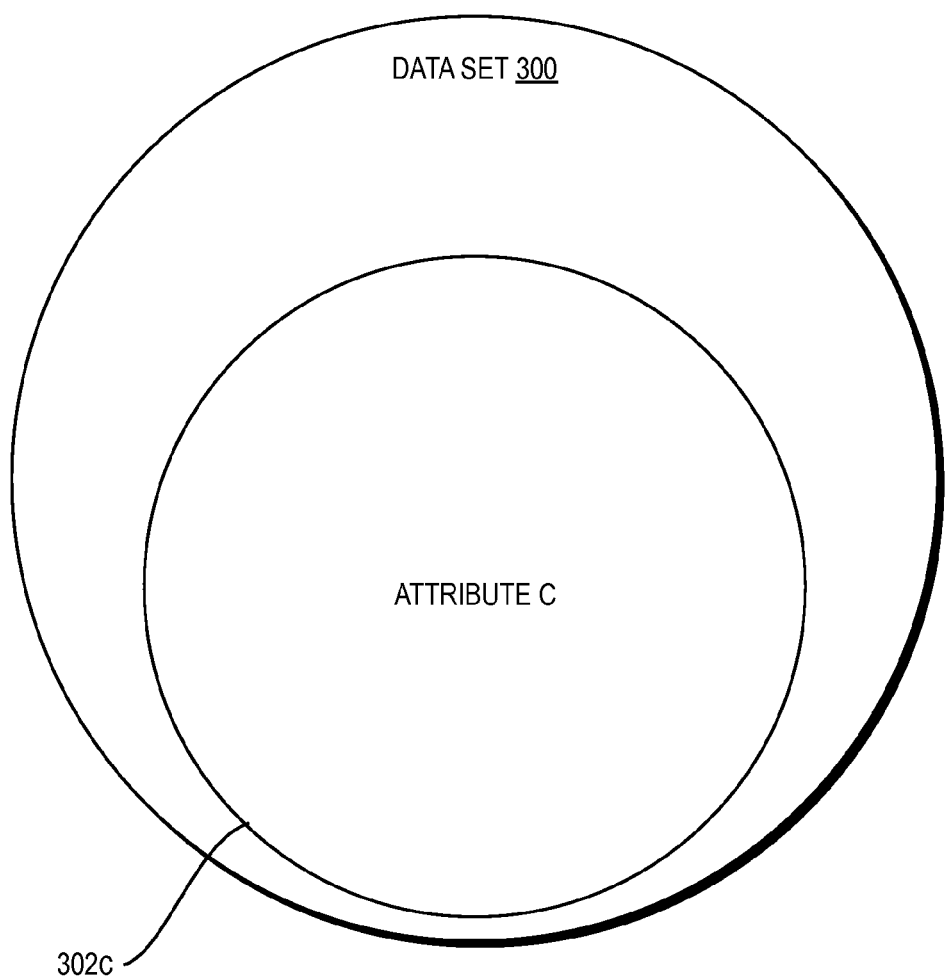

Finally, the attribute set identifier 108 uses attribute set definition 106*c* to identify attribute set 110*c* as the subset of the data set 102 which possesses attribute C. A graphical illustration of attribute set 110*c* is shown in FIG. 3D as attribute set 302*c*. Assume for purposes of example that attribute set 302*c* contains those 500 elements of data set 300 which possess attribute C. The portion of data set 300 in FIG. 3D which is not within attribute set 302*c* are those 500 elements of data set 300 which do not possess attribute C.

The attribute sets 110*a-c* may be stored and represented in any way. For example, each of the attribute sets 110*a-c* may be represented as a data structure containing pointers to the corresponding element(s) in the data set 102. As another example, the elements 104*a-n* in the data set may be tagged to indicate the attribute set(s) of which they are members. Embodiments of the present invention, however, are not limited to any particular technique for storing and representing the attribute sets 110*a-c*.

Attributes may be assigned weights, which may be specified in any way, such as in percentages, as decimals, or as a sequence of values (e.g., 1, 2, 3), where the weight of any number in the sequence is defined by the position of the number in the sequence. Assume for purposes of the following discussion, and merely as an example, that attribute A has a weight of 40%, that attribute B has a weight of 30%, and that attribute C has a weight of 50%. As this example illustrates, weights may, but need not, sum to 100%. In the following discussion, the weight of a particular attribute X will be referred to as $W_X$.

Referring again to FIG. 1A, attribute weights 112*a-c* are shown which correspond to attributes A, B, and C, respectively. The weights 112*a-c* may be created and provided to the system 100 in any of a variety of ways. For example, a user may input each of the weights 112*a-c*. The techniques disclosed herein, however, may be used regardless of how the weights 112*a-c* are created and provided to the system 100.

The attribute weights 112*a-c* may be used for a variety of purposes. For example, the attribute weights 112*a-c* may be used to reduce the number of elements in each of the attribute sets 110*a-c* as follows, thereby producing reduced attribute sets 116*a-c*, respectively (also referred to herein as "filtered" attribute sets). Note, however, that such reduction is optional. Therefore, any functions disclosed herein as being performed on the reduced attribute sets 116*a-c* may alternatively be performed on the original (non-reduced) attribute sets 110*a-c*.

Before describing how the attribute sets 110*a-c* are reduced to produce the reduced attribute sets 116*a-c*, note that some attributes may be sortable, while other attributes may be non-sortable. An attribute is sortable if it can be added to a list in a particular order according to an internal hierarchy or ranking mechanism. An attribute is non-sortable if it cannot be added to a list in any particular order, due to lack of an internal hierarchy or ranking mechanism.

For example, an attribute representing cost may be sortable, while an attribute representing whether a person is an employee may not be sortable. Attributes which are sortable may be sorted in either ascending or descending order. Whether a particular attribute should be sorted in ascending or descending order may be specified, for example, as part of the corresponding attribute set definition. For example, if attribute A is a sortable attribute, then attribute set definition 106a may specify whether elements in the corresponding attribute set 110a should be sorted in ascending or descending order. As another example, the sort order (direction) may be specified by the definition of the attribute itself (not shown), such that each attribute is always sorted in the order specified by the attribute's definition.

Figure 1B:
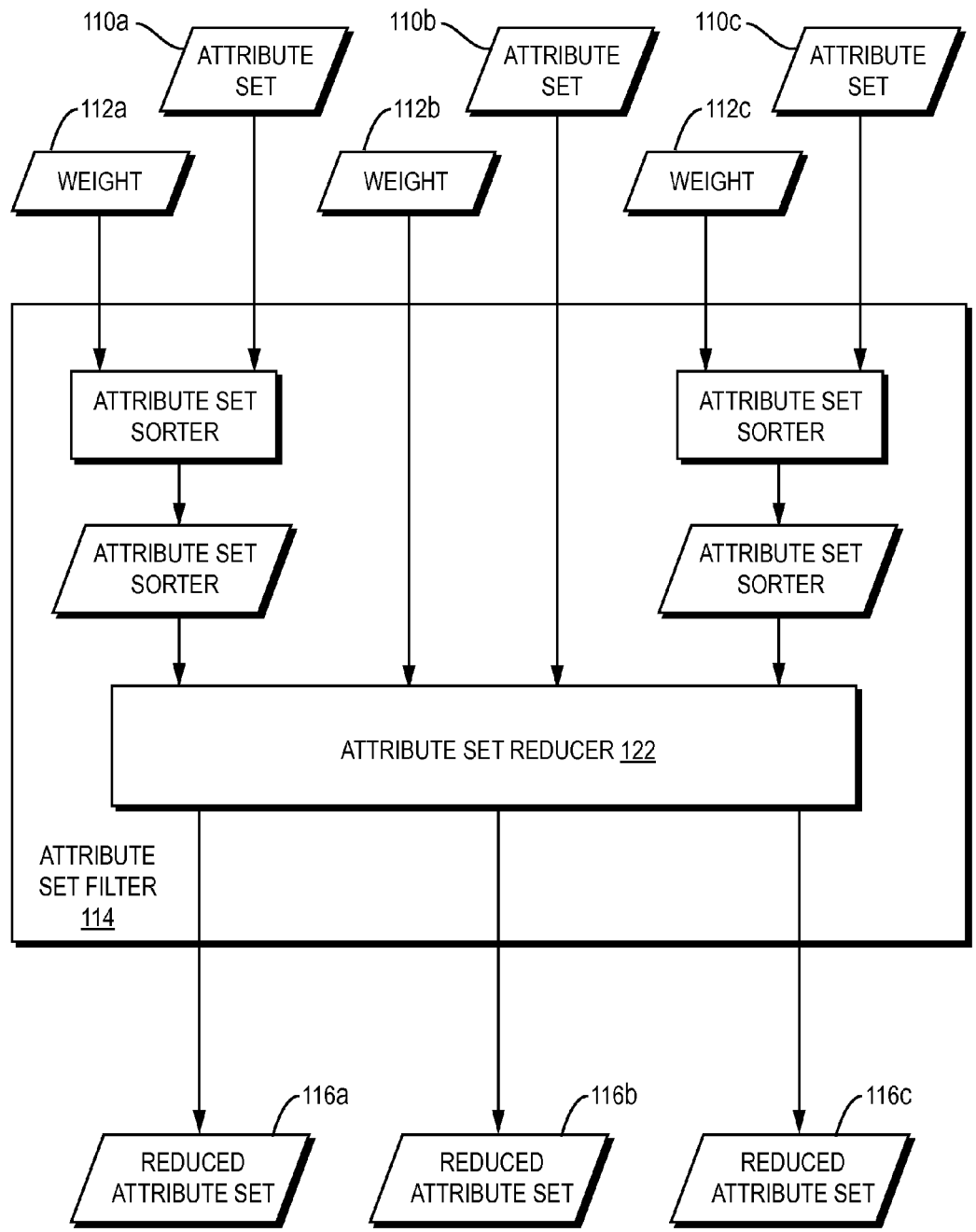
FIG. 1B is a dataflow diagram of a system for removing elements from attribute sets to produce reduced attribute sets according to one embodiment of the present invention.

Referring to FIG. 1B and FIG. 2A, an attribute set filter 114 may produce the reduced attribute sets 116a-c as follows. For each attribute set S (FIG. 2A, step 208), the attribute set filter 114 determines whether the attribute associated with set S is sortable or non-sortable (step 210). If the attribute is sortable, then an attribute set sorter 118 sorts the elements in the set by attribute value (either in ascending or descending order, as appropriate) (step 212) to produce a sorted attribute set. If the attribute is non-sortable, no action is taken.

For example, referring to FIG. 1B, if it is assumed that attribute A is a sortable attribute, then the attribute set sorter 118 sorts attribute set 110a to produce sorted attribute set 120a. If it is assumed that attribute B is a non-sortable attribute, then attribute set sorter 118 takes no action on attribute set 110b. Finally, if it is assumed that attribute C is a sortable attribute, then attribute set sorter 118 sorts attribute set 110c to produce sorted attribute set 120c.

Next, the attribute set filter 114 removes, from set S, a number of elements based on the weight associated with set S (step 214). The result is a reduced attribute set. In particular, if the weight associated with a particular attribute set S is $W_S$, then the bottom $(100-W_S)$ % of set S may be removed from set S to produce the corresponding reduced attribute set. Assuming that the weight associated with attribute A is 40%, the bottom 60% of sorted attribute set 120a may be removed from sorted attribute set 120a to produce reduced attribute set 116a. If attribute set 110a contains 500 elements, reduced attribute set 116a contains 200 elements.

Assuming that the weight associated with attribute B is 30%, the bottom 50% of (original) attribute set 110b may be removed from attribute set 110b to produce reduced attribute set 116b. If attribute set 110b contains 500 elements, reduced attribute set 116b contains 150 elements.

Finally, assuming that the weight associated with attribute C is 60%, the bottom 40% of sorted attribute set 120c may be removed from sorted attribute set 120c to produce reduced attribute set 116c. If attribute set 110c contains 500 elements, reduced attribute set 116c contains 250 elements.

Figure 3E:
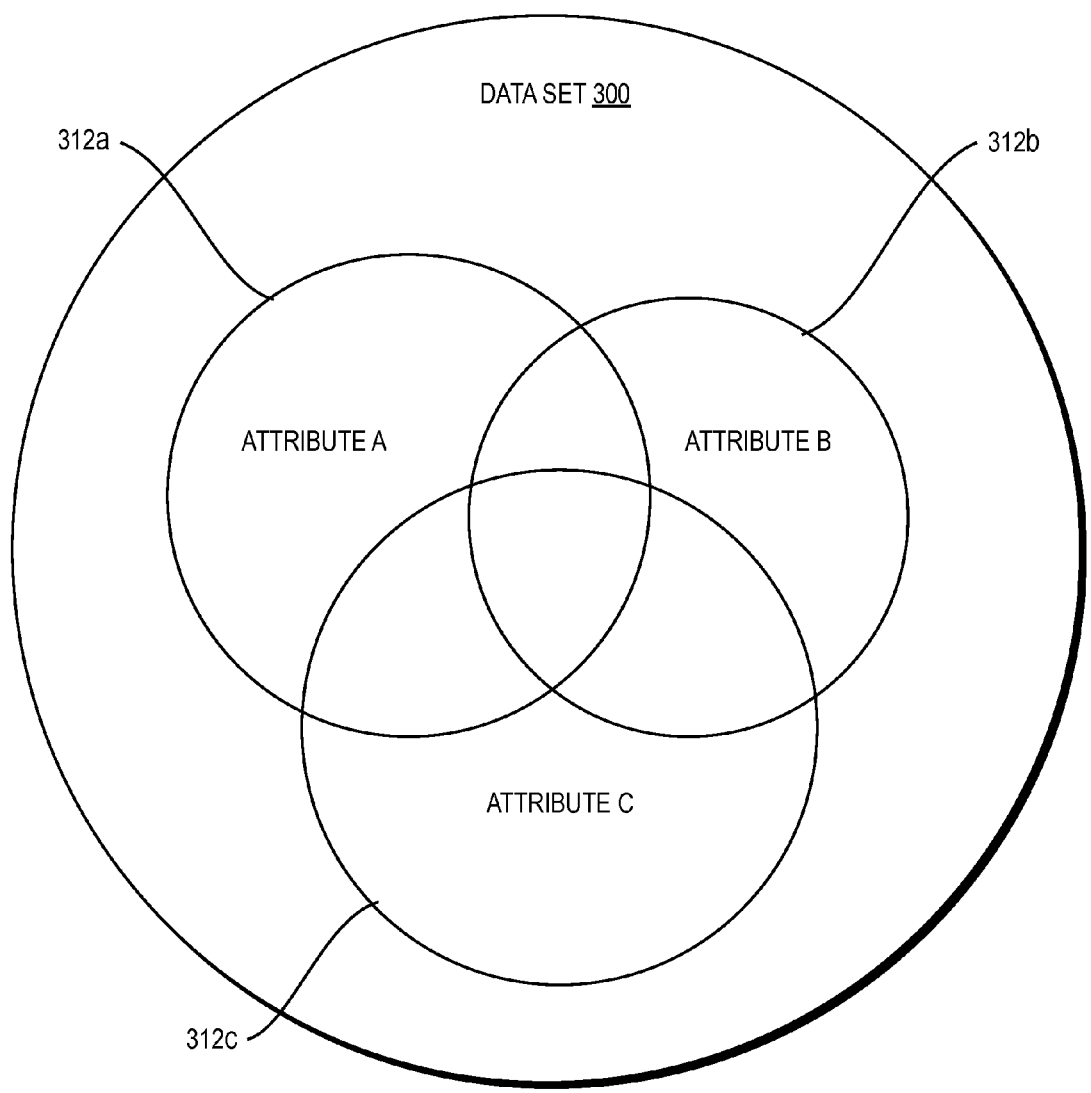
FIGS. 3E-3F are diagrams of overlapping regions of reduced attribute sets according to one embodiment of the present invention.

Steps 210-214 are repeated for each attribute set (step 216) in the manner described above. The end result is the set of reduced attribute sets 116a-c shown in FIG. 1A. These reduced attribute sets 116a-c are illustrated graphically in FIG. 3E as reduced attribute sets 312a-312c, respectively. Note that the sizes of the circles in FIG. 3E are proportional to the sizes of the corresponding reduced sets.

Figure 1C:
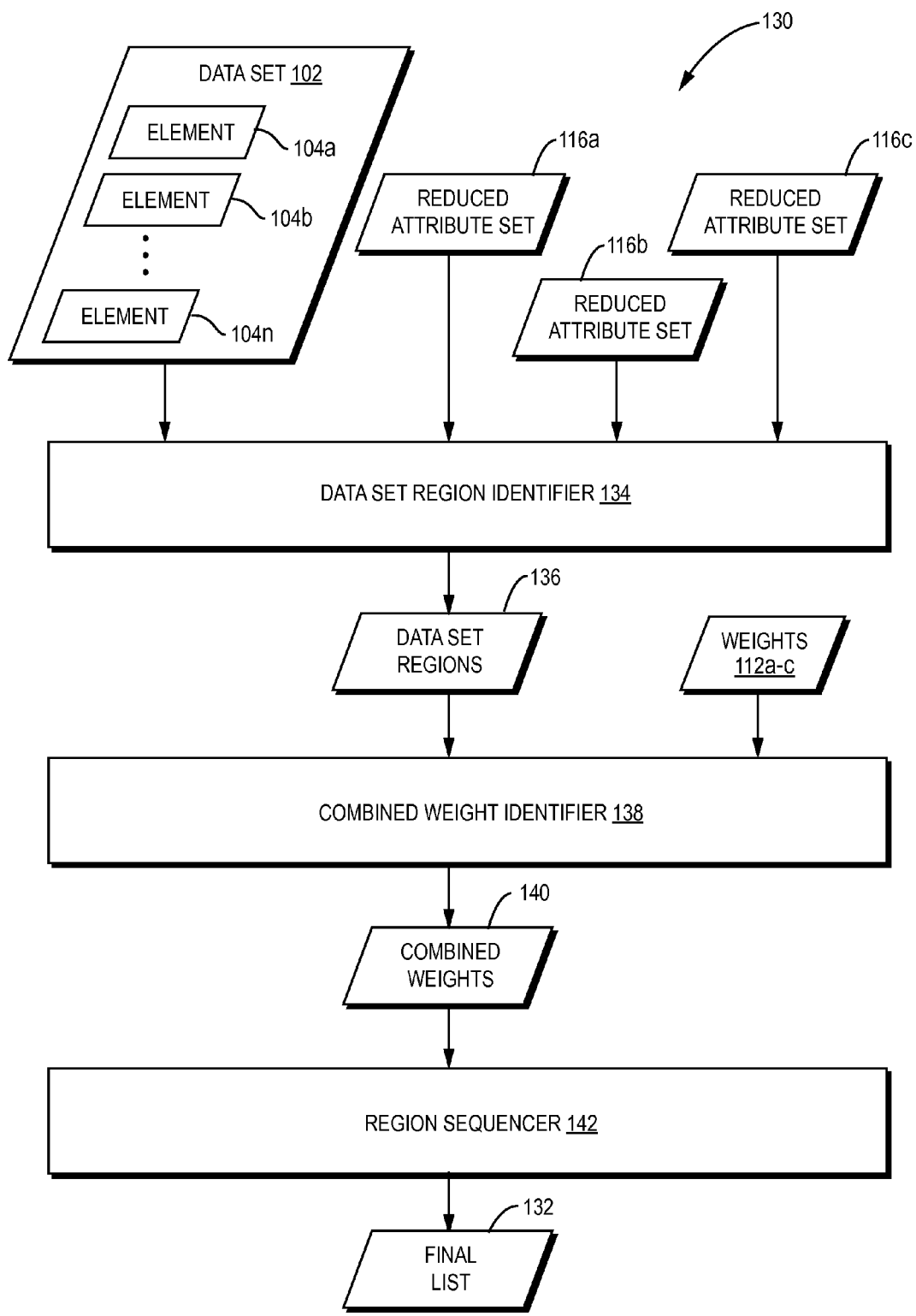
FIGS. 1C and 1D are dataflow diagrams of systems for ordering elements into a final list according to one embodiment of the present invention.
Figure 2B:
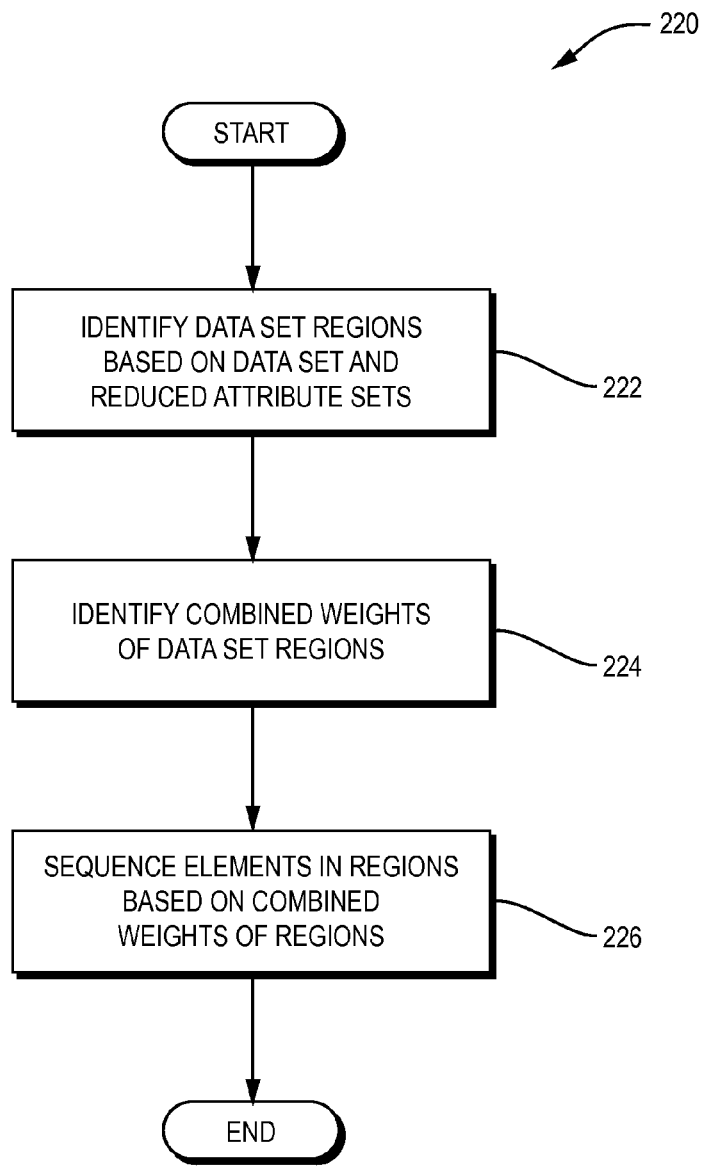
FIG. 2B is a flowchart of a method performed by the system of FIG. 1C according to one embodiment of the present invention.

Now referring to FIG. 1C and FIG. 2B, the reduced attribute sets 116a-c may be used to order the elements 104a-n in the data set 102 into a final list 130. In general, the system 130 of FIG. 1C and the method 220 of FIG. 2B arrange some or all of the elements 104a-n of the data set 102 into a sequence, within the final list 132, that is based on the attributes possessed by the elements 104a-n and the weights of those attributes. The weights of all attributes possessed by an element may be combined together to produce a combined weight for that element. In general, the system 130 and method 220 tend to position elements having relatively high combined weights closer to the top (beginning) of the final list 132 than elements having relatively low combined weights. Examples of ways in which such ordering may be performed will now be described in more detail.

Figure 3F:
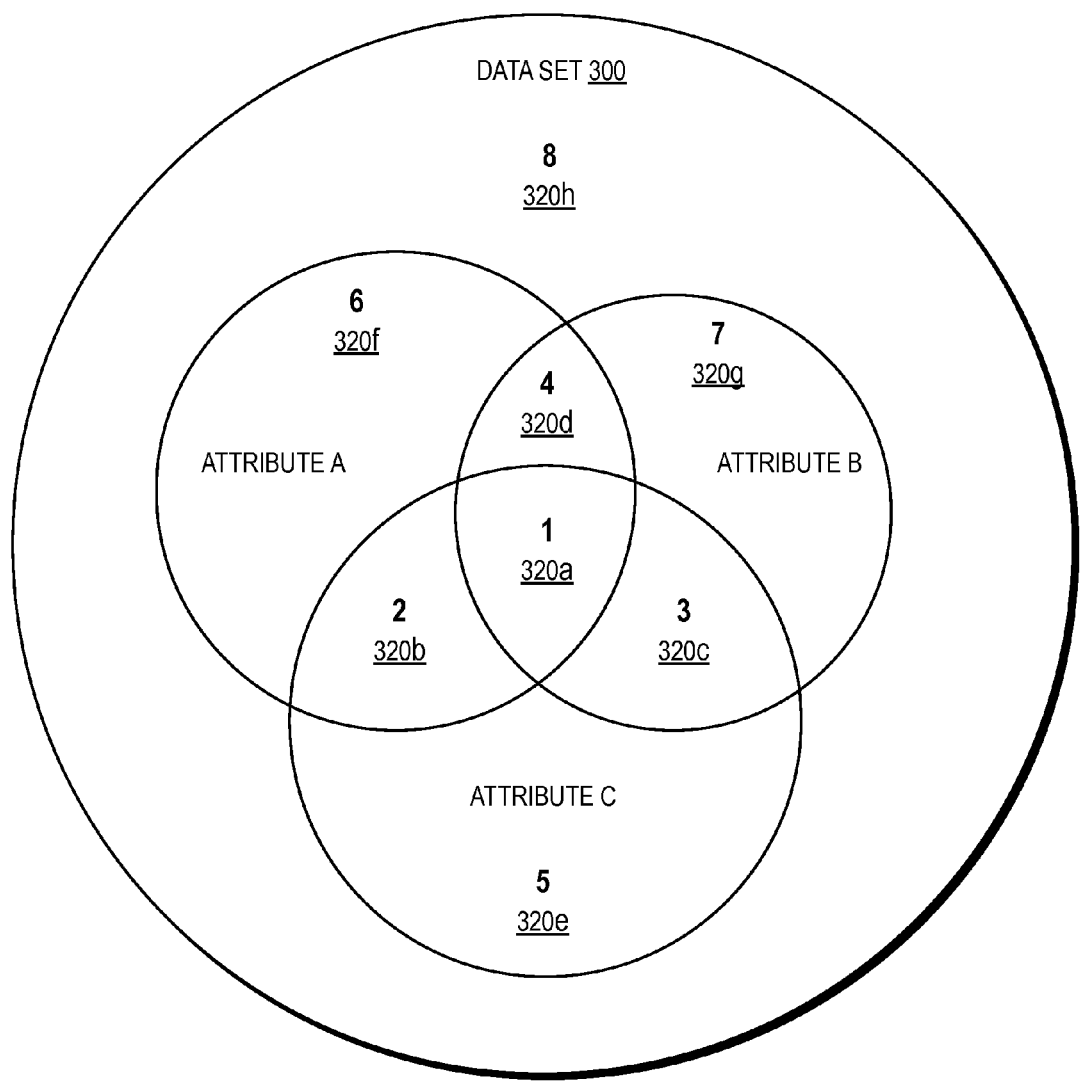

Recall that the reduced attribute sets 116a-c may overlap with each other. An example of such overlap is illustrated in FIG. 3F. As shown in FIG. 3F: (1) region 320a contains the elements from the data set 300 which have attributes A, B, and C; (2) region 320b contains the elements from the data set 300 which have attributes A and C but not B; (3) region 320c contains the elements from the data set 300 which have the attributes B and C but not A; (4) region 320d contains the elements from the data set 300 which have the attributes A and B but not C; (5) region 320e contains the elements from the data set 300 which have attribute C but not A or B; (6) region 320f contains the elements from the data set 300 which have attribute A but not B or C; (7) region 320g contains the elements from the data set 300 which have attribute B but not A or C; and (8) region 320h contains the remaining elements from the data set, which do not have any of the attributes A, B, or C. The particular kind and extent of overlap shown in FIG. 3F is merely an example and does not constitute a limitation of the present invention.

Referring again to FIGS. 1C and 2B, a data set region identifier 134 may identify all overlapping and non-overlapping (intersecting) regions (subsets) within the data set, based on the data set 102 itself and the reduced attribute sets 116a-c (FIG. 2, step 222). (As mentioned above, if filtering was not previously applied to the original attribute sets 110a-c, then the data set region identifier 134 may be applied to the original attribute sets 110a-c instead of the reduced attribute sets 116a-c.) The resulting regions, each of which corresponds to a distinct combination of zero or more of the attributes which define the reduced attribute sets 116a-c, are referred to herein as data set regions 136. The regions 320a-h shown in FIG. 3F are an example of the data set regions 136. The data set regions 136 may be stored and represented in any manner which makes it possible to use the data set regions 136 to identify the region to which any particular element in the data set 300 belongs.

A combined weight identifier 138 identifies a combined weight for each of the data set regions 136 based on the data set regions 136 and the attribute weights 112a-c (step 224). For example, for each region R in the regions 136, the combined weight identifier 138 may identify a combined weight for region R by summing the (zero or more) weights of all of the attributes associated with region R. For example, assuming again that the weights of attributes A, B, and C are 40%, 30%, and 50%, respectively, then the combined weights 140 of the regions 320a-h in FIG. 3F are given by Table 1.

TABLE 1

| Region | Associated Attributes | Combined Weight |
|---|---|---|
| 320a | A, B, C | 120% |
| 320b | A, C | 90% |
| 320c | B, C | 80% |
| 320d | A, B | 70% |
| 320e | C | 50% |
| 320f | A | 40% |
| 320g | B | 30% |
| 320h | None | 0% |

As will be described in more detail below, the regions 320a-h may be processed in descending order of their combined weights. This may involve first sorting the combined weights 140 and/or sorting the data set regions 136. Alternatively, however, the elements in the regions 136 may simply be processed in the appropriate order without first performing any sorting.

A region sequencer 142 (FIG. 1C) then orders the elements in the regions 136 into the final list 132 in a sequence that is dictated by the combined weights 140 of the regions (FIG. 2B, step 226). More specifically, referring to FIGS. 1D and 2C, a system 150 and method 250 are shown for using the region sequencer 142 to produce the final list 132 from the regions 136 based on the combined weights 140.

Figure 2C:
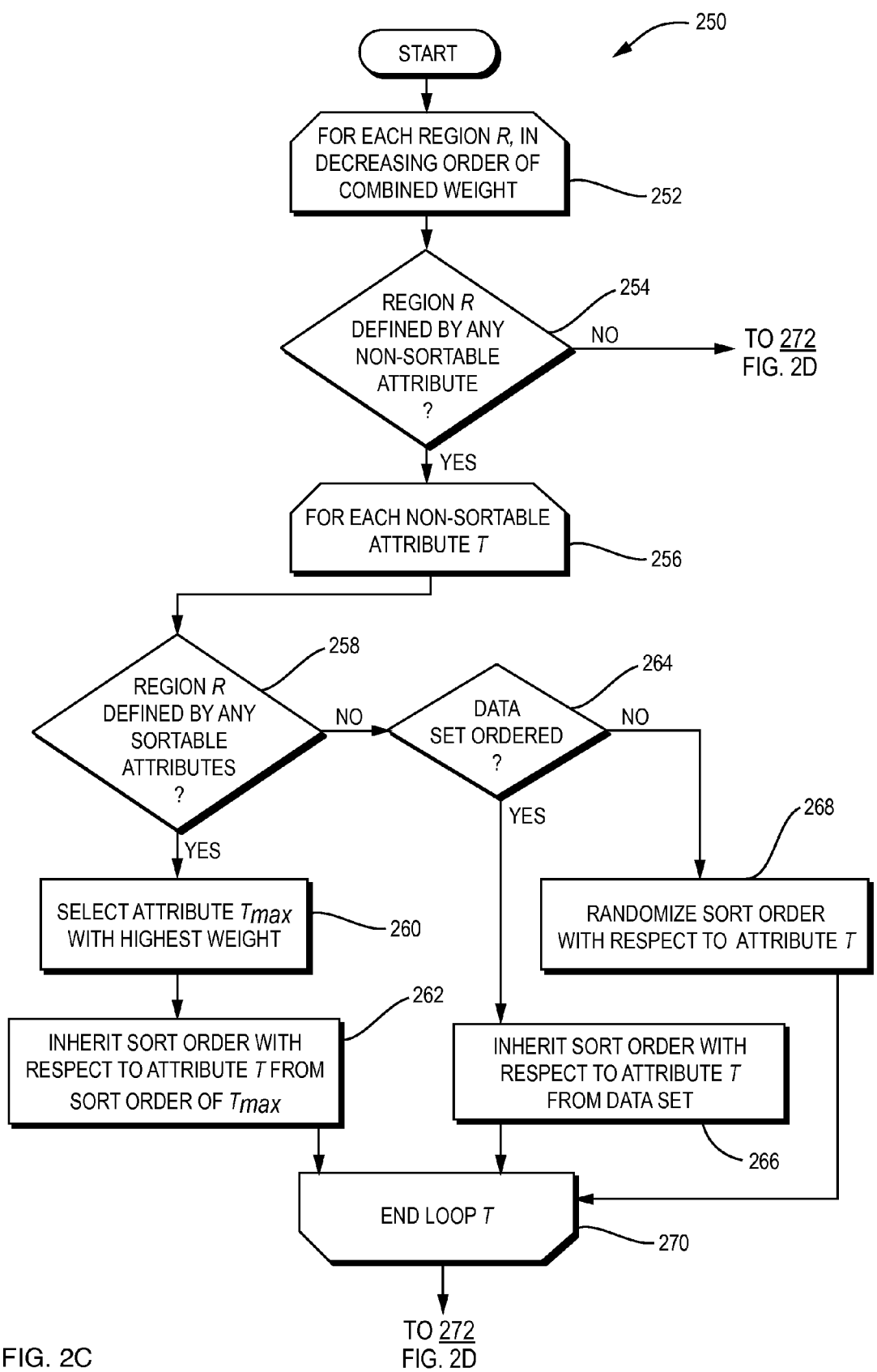
FIGS. 2C and 2D are flowcharts of methods for ordering elements into a final list according to one embodiment of the present invention.

The region sequencer 142 processes each region R in the regions 136 in decreasing order of their combined weights (FIG. 2C, step 252). In the example of Table 1, the regions 136 would be processed in the following order: 320a, 320b, 320c, 320d, 320e, 320f, 320g, and 320h.

Within each of the regions 136, elements having sortable attributes are still sorted in the orders created previously in step 212 of FIG. 2A. For a particular region, the elements may have different sort orders (sequences), one for each sortable attribute possessed by the elements. For a simple example, assume that region 320a in FIG. 3F contains just three elements, each of which has attributes A, B, and C. In the method 200 of FIG. 2A, step 212 was previously applied to these three elements based on attribute A to produce a sort order corresponding to attribute A. Similarly, step 212 was previously applied to these three elements based on attribute C to produce a sort order corresponding to attribute C. Step 212 was not applied to these three elements based on attribute B because, in this example, attribute B is not a sortable attribute. Assume for purposes of example that the resulting sort orders of these three elements was as shown in Table. 2.

TABLE 2

| Attribute A Sort Order | Attribute B Sort Order | Attribute C Sort Order |
|---|---|---|
| Element 2 | <Unsorted> | Element 1 |
| Element 1 | <Unsorted> | Element 3 |
| Element 3 | <Unsorted> | Element 2 |

Although each column of Table 2 corresponds to the same three elements, Table 2 illustrates that such a set of elements may be sorted in different orders based on different attributes. In particular, in this example the three elements have been sorted in a different order based on Attribute A than for Attribute C. Furthermore, because Attribute B in this example is a non-sortable attribute, all three elements are listed as <Unsorted> in Table 2.

As Table 2 illustrates, these differing sort orders of the same set of elements must be reconciled before the elements may be placed into the final list 132. One way in which this reconciliation may be performed is as follows.

A non-sortable attribute orderer 152 (FIG. 1D) then orders any non-sortable attributes in the regions 136 to produce fully sorted regions 154 as follows. If the current region R being processed is defined by any non-sortable attributes (FIG. 2C, step 254), then for each non-sortable attribute (step 256) the following is performed. In the case of region 320a of FIG. 3F, as represented by Table 2, attribute B is a non-sortable attribute, so the "Yes" branch of step 254 would be followed in this case.

If region R is also defined by any sortable attributes (step 258), then the sortable attribute of region R with the highest attribute weight is selected (step 260). For example, in the case of region 320a of FIG. 3F, as represented by Table 2, region 320a is also defined by sortable attributes A and C, so the "Yes" branch of step 258 would be followed in this case, in which case attribute C would be selected by step 260 because its weight (60%) is higher than the weight of attribute A (40%).

The sort order of elements in region R with respect to the current non-sortable attribute is then inherited from the sort order of elements in region R with respect to the sortable attribute selected in step 260 (step 262). In the current example, the sort order of elements in region 320a with respect to non-sortable attribute B would be inherited from the sort order of elements in region 320a with respect to sortable attribute C, resulting in the sort order shown in Table 3.

TABLE 3

| Attribute A Sort Order | Attribute B Sort Order | Attribute C Sort Order |
|---|---|---|
| Element 2 | Element 1 | Element 1 |
| Element 1 | Element 3 | Element 3 |
| Element 3 | Element 2 | Element 2 |

Figure 1D:
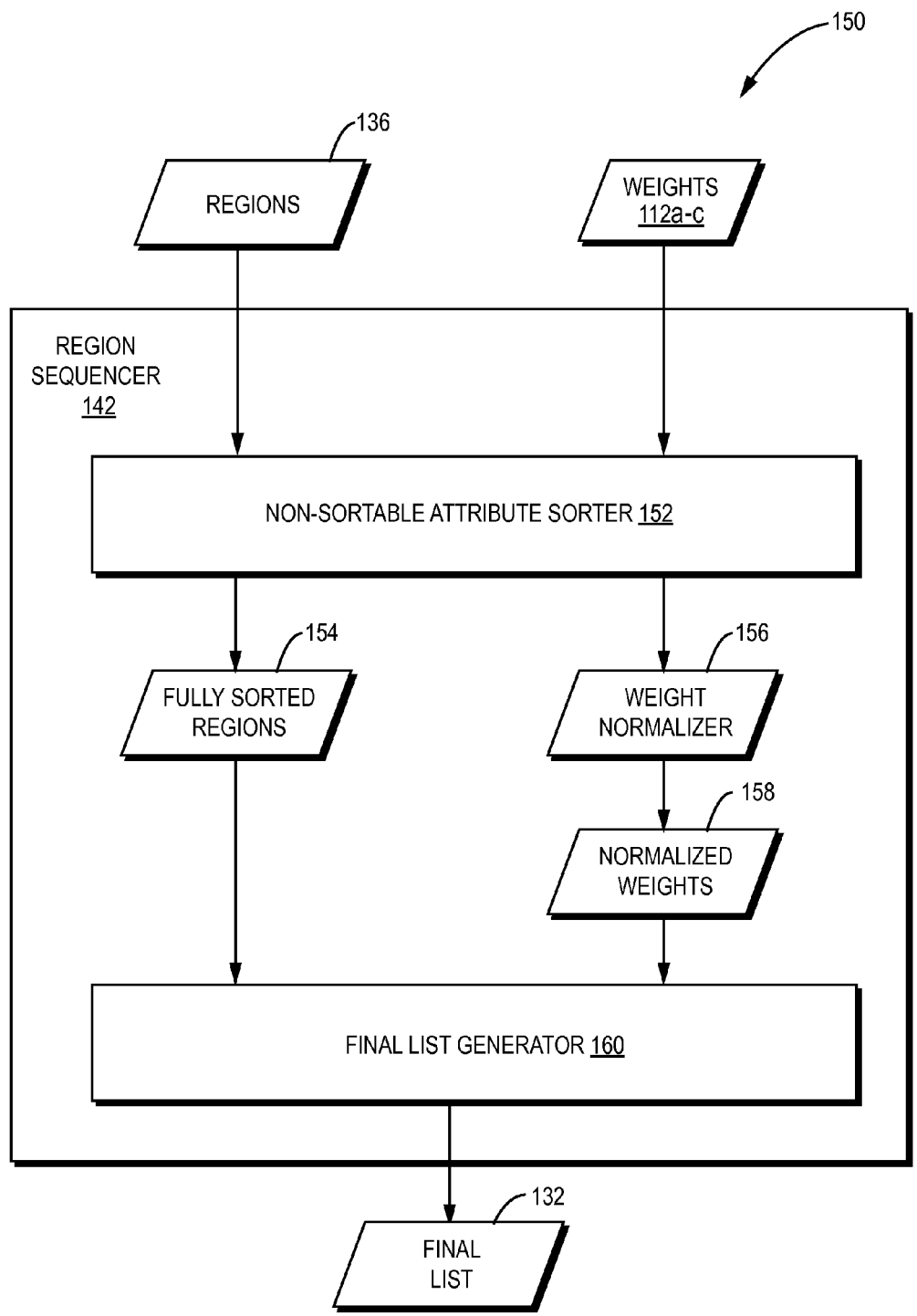
Figure 2D:
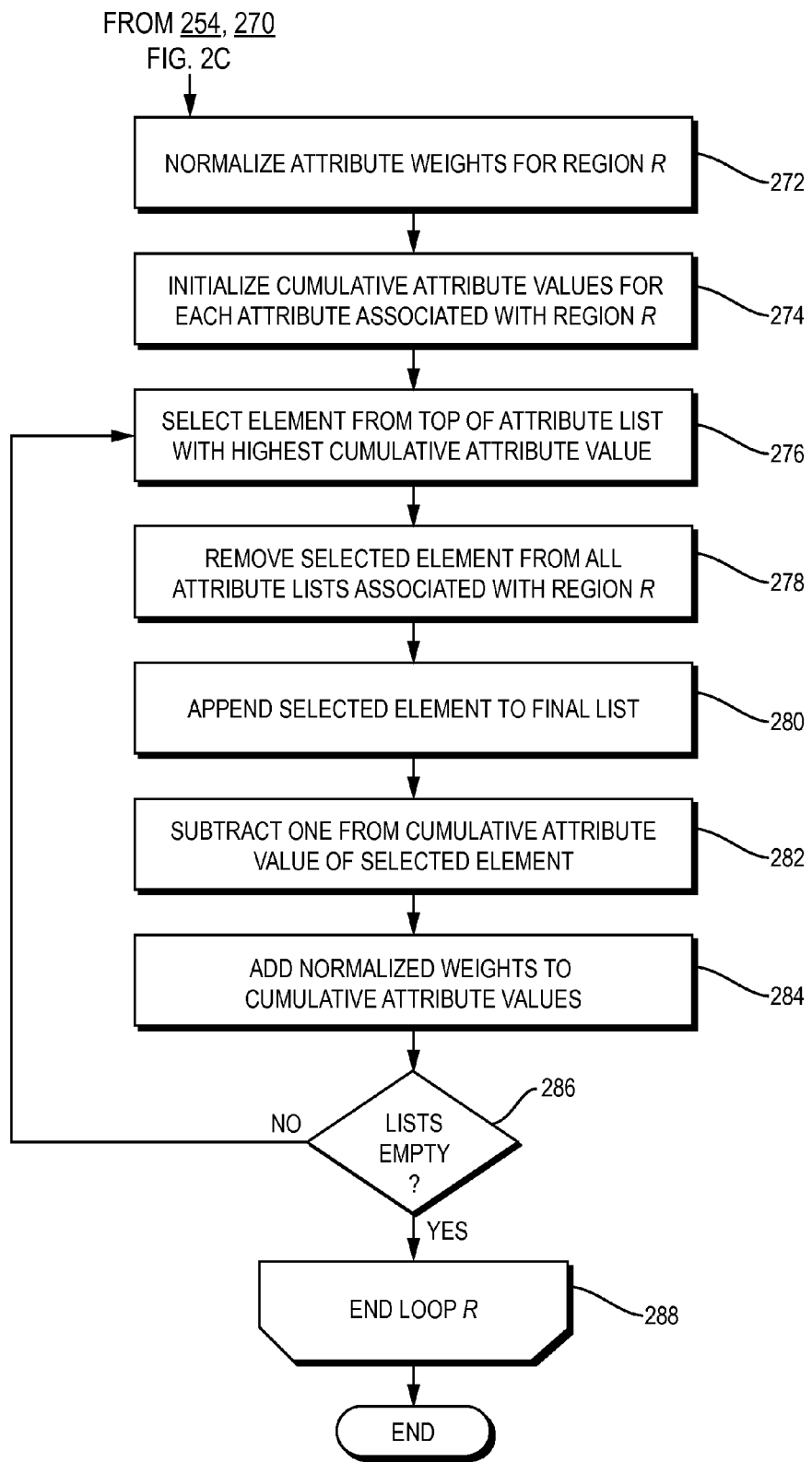

If region R is not defined by any non-sortable attributes (step 258), then: (1) if the data set 102 itself is sorted (step 264), then the sort order of elements in region R with respect to the current non-sortable attribute is inherited from the sort order of the data set 102 (step 266); (2) if the data set 102 itself is not sorted (step 264), then the elements in region R are randomized with respect to the current non-sortable attribute (step 268). The remaining steps described with respect to FIGS. 1D and 2D are performed in connection with the fully sorted regions 154, in which an order is associated with all elements in each region in connection with all attributes that define the region, as in the example illustrated by Table 3.

An attribute weight normalizer 156 (FIG. 1D) normalizes the weights of the attributes associated with region R to produce normalized weights 158 (step 272). Each region R, in other words, has its own set of normalized weights. In the case of region 320a, for example, in which the weights of the associated attributes A, B, and C, are 40%, 30%, and 50%, respectively, the normalized attribute weights for region 320a are 0.8 (80%), 0.6 (60%), and 1.0 (100%), respectively.

Within each region R, elements are inserted from region R into the final list 132 in a sequence that reflects the relative weights of the attributes possessed by those elements. More specifically, in one embodiment of the present invention, a final list generator 160 initializes cumulative attribute values for each attribute associated with region R (FIG. 2D, step 274). In the case of region 320a, which is associated with attributes A, B, and C, cumulative attribute values $A_{cum}$, $B_{cum}$, and $C_{cum}$, respectively, may be initialized to values of 0.8, 0.6, and 1.0, respectively (namely, to the normalized weights of the corresponding attributes).

The attribute set associated with region R which has the highest associated cumulative attribute value is identified, and the element at the top (beginning) of the identified attribute set is selected (step 276). For example, if $A_{cum}=0.8$, $B_{cum}=0.6$, and $C_{cum}=1.0$, then $C_{cum}$ has the highest associated cumulative attribute value, and the element at the top of the corresponding attribute set (namely, element 1 in Table 3) would be selected from attribute set 302c.

The selected element is removed from all of the attribute sets associated with region R (step 278). In this example, Element 1 would be removed from the lists represented by the three columns of Table 3, so that Element 1 is not selected again for inclusion in the final list 132.

The selected element is appended to the final list 132 (step 280). In this case, Element 1 would be appended to the (currently empty) final list 132, thereby becoming the first element in the final list 132.

The value of the cumulative attribute value which was previously identified in step 276 as the highest cumulative attribute value is decreased by 1.0 (step 282). In this example, 1.0 would be subtracted from $C_{cum}$ to obtain a new value for $C_{cum}$ of 0.

Each of the remaining cumulative attribute values is increased by its associated normalized weight (step 284). For example, 0.8 is added to $A_{cum}$ to obtain a new value of 1.6, and 0.6 is added to $B_{cum}$ to obtain a new value of 1.2.

If the attribute set lists corresponding to region R are not empty (step 286), then steps 276-284 are repeated to continue filling the final list 132 with elements from region R in a sequence dictated by the weights of attributes associated with region R. Once the lists associated with region R are empty (step 286), processing of region R is complete, and the remaining regions are processed, in decreasing order of their combined weights (step 288). Once all of the regions 136 have been processed in this way, the final list 132 is complete and contains an ordered list of the elements from the original data set 300, ordered according to the multiple criteria specified by the attribute sets 110*a-c* and their associated weights 112*a-c*.

Embodiments of the present invention have a variety of advantages. For example, embodiments of the present invention may be used to order elements into a list quickly based on any number of criteria. In contrast, many existing systems are limited to ordering elements based on a single criterion. In real-world applications, however, such as scheduling of staff in a hospital or other facility, it is often necessary to order elements based on not only two criteria, but a much larger number of criteria. Embodiments of the present invention can perform such ordering both accurately and quickly.

For example, existing scheduling algorithms typically use a "round-robin" scheduling approach, which requires the system to cycle through all personnel to be scheduled every time a change to the schedule is required. This process can be very resource intensive and slow as a result. In contrast, embodiments of the present invention may be used to pre-filter, pre-blend, and pre-sort subsets of the data set before mixing, which significantly reduces the amount of processing time needed to produce a schedule. In practice, this can result in an increase in speed of an order of magnitude or more over existing systems, or alternatively a decrease in required computing resources (e.g., processor cycles) of an order of magnitude or more over existing systems.

Furthermore, as the examples above illustrate, embodiments of the present invention can create an ordered list based on a wide variety of criteria. For example, some criteria may be sortable, while others may be non-sortable. Embodiments of the present invention may order a list based on any combination of both sortable and non-sortable criteria. This is yet another feature of embodiments of the present invention which provide it with greater flexibility than existing systems.

Furthermore, embodiments of the present invention may order elements which contain any combination of attributes. As the examples above illustrate, any particular element may have zero, one, two, three, or more attributes. As mentioned above, each such attribute may be non-sortable or sortable. Sorting may be performed in either ascending or descending order. These are further examples of ways in which embodiments of the present invention provide greater flexibility than existing systems.

In addition, as the examples above illustrate, different weights may be assigned to different attributes. Such attribute weights may be used to influence the order of individual elements in the final list based on the attributes possessed by such elements. The individual attribute weights may be adjusted in any manner desired to affect the order of the final list. This is yet another way in which embodiments of the present invention provide greater flexibility than existing systems.

When applied to a real-world application, such as scheduling of nurses at a hospital, the techniques disclosed herein may be used to quickly, efficiently, and continuously maximize the fit between the preferences of nurses and the schedules assigned to them. The multiple attributes disclosed herein may be used to implement multiple criteria specified by the hospital, to represent characteristics such as cost and seniority, according to the priorities of the hospital. By enabling the hospital to produce schedules which align better both with the hospital's goals and the nurse's needs, embodiments of the present invention may be used to increase employee satisfaction and retention.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

The techniques described above may be implemented, for example, in hardware, software tangibly embodied in a computer-readable medium (such as in non-transitory signals stored on such a computer-readable medium), firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

What is claimed is:

1. A computer-implemented method for ordering a plurality of elements, wherein each of the plurality of elements has at least one corresponding attribute, the method comprising:
   (A) identifying a first subset of the plurality of elements associated with a first attribute by selecting, from among the plurality of elements, at least one element having the first attribute;
   (B) identifying a first weight associated with the first attribute;
   (C) removing, from the first subset, a number of elements based on the first weight, to produce a first reduced subset of the plurality of elements;
   (D) identifying a second subset of the plurality of elements associated with a second attribute by selecting, from among the plurality of elements, at least one element having the second attribute;
   (E) identifying a second weight associated with the second attribute, wherein the second weight differs from the first weight;
   (F) removing, from the second subset, a number of elements based on the second weight, to produce a second reduced subset of the plurality of elements;
   (G) identifying a plurality of regions, each of which corresponds to a distinct combination of zero or more of the first and second attributes, wherein the plurality of regions includes a first region including a first and second element in the plurality of elements and a second region including a third and fourth element in the plurality of elements;
   (H) for each region R in the plurality of regions, identifying a corresponding weight sum for region R comprising a sum of the weights of the zero or more attributes corresponding to R;
   (I) for each region R, ordering elements within region R to produce an ordered list of elements corresponding to region R, thereby producing a plurality of ordered lists of elements corresponding to the plurality of regions; and
   (J) combining the plurality of ordered lists of elements, in decreasing order of the weight sums corresponding to the plurality of ordered lists, to produce an ordered list of the plurality of elements.

2. The method of claim 1, wherein each element in the first subset has a corresponding value, and wherein (C) comprises:
   (C)(1) sorting the first subset by the values of its elements to produce a sorted first subset; and
   (C)(2) removing, from the bottom of the sorted first subset, a number of elements based on the first weight, to produce a first reduced subset of the plurality of elements.

3. The method of claim 2, wherein the first attribute is associated with a sort direction, and wherein (C)(1) comprises sorting the first subset in the sort direction associated with the first attribute.

4. The method of claim 1, further comprising:
   (K) identifying a third subset of the plurality of elements associated with a third attribute by selecting, from among the plurality of elements, at least one element having the third attribute;
   (L) identifying a third weight associated with the third attribute;
   (M) removing, from the third subset, a number of elements based on the third weight, to produce a third reduced subset of the plurality of elements; and
   wherein (G) comprises identifying a plurality of regions, each of which corresponds to a distinct combination of zero or more of the first, second, and third attributes.

5. A non-transitory computer-readable medium having computer-readable instructions tangibly stored thereon, wherein the computer-readable instructions are executable by a computer processor to perform a method for ordering a plurality of elements, wherein each of the plurality of elements has at least one corresponding attribute, the method comprising:
   (A) identifying a first subset of the plurality of elements associated with a first attribute by selecting, from among the plurality of elements, at least one element having the first attribute;
   (B) identifying a first weight associated with the first attribute;
   (C) removing, from the first subset, a number of elements based on the first weight, to produce a first reduced subset of the plurality of elements;
   (D) identifying a second subset of the plurality of elements associated with a second attribute by selecting, from among the plurality of elements, at least one element having the second attribute;
   (E) identifying a second weight associated with the second attribute, wherein the second weight differs from the first weight;
   (F) removing, from the second subset, a number of elements based on the second weight, to produce a second reduced subset of the plurality of elements; and
   (G) identifying a plurality of regions, each of which corresponds to a distinct combination of zero or more of the first and second attributes, wherein the plurality of regions includes a first region including a first and second element in the plurality of elements and a second region including a third and fourth element in the plurality of elements;
   (H) for each region R in the plurality of regions, identifying a corresponding weight sum for region R comprising a sum of weights of the zero or more attributes corresponding to R;
   (I) for each region R, ordering elements within region R to produce an ordered list of elements corresponding to region R, thereby producing a plurality of ordered lists of elements corresponding to the plurality of regions; and
   (J) combining the plurality of ordered lists of elements, in decreasing order of the weight sums corresponding to the plurality of ordered lists, to produce an ordered list of the plurality of elements.

6. The non-transitory computer-readable medium of claim 5, wherein each element in the first subset has a corresponding value, and wherein (C) comprises:
   (C)(3) sorting the first subset by the values of its elements to produce a sorted first subset; and
   (C)(4) removing, from the bottom of the sorted first subset, a number of elements based on the first weight, to produce a first reduced subset of the plurality of elements.

7. The non-transitory computer-readable medium of claim 6, wherein the first attribute is associated with a sort direction, and wherein (C)(1) comprises sorting the first subset in the sort direction associated with the first attribute.

8. The non-transitory computer-readable medium of claim 5, wherein the method further comprises:
- (K) identifying a third subset of the plurality of elements associated with a third attribute by selecting, from among the plurality of elements, at least one element having the third attribute;
- (L) identifying a third weight associated with the third attribute;
- (M) removing, from the third subset, a number of elements based on the third weight, to produce a third reduced subset of the plurality of elements; and
- wherein (G) comprises identifying a plurality of regions, each of which corresponds to a distinct combination of zero or more of the first, second, and third attributes.

9. A computer-implemented method for ordering a plurality of elements, wherein each of the plurality of elements has at least one corresponding attribute, the method comprising:
- (A) identifying a first subset of the plurality of elements associated with a first attribute by selecting, from among the plurality of elements, at least one element having the first attribute;
- (B) identifying a first weight associated with the first attribute;
- (C) identifying a second subset of the plurality of elements associated with a second attribute by selecting, from among the plurality of elements, at least one element having the second attribute;
- (D) identifying a second weight associated with the second attribute, wherein the second weight differs from the first weight;
- (E) identifying a plurality of regions, each of which corresponds to a distinct combination of zero or more of the first and second attributes, wherein the plurality of regions includes a first region including a first and second element in the plurality of elements and a second region including a third and fourth element in the plurality of elements;
- (F) for each region R in the plurality of regions, identifying a corresponding weight sum for region R comprising a sum of the weights of the zero or more attributes corresponding to R;
- (G) for each region R, ordering elements within region R to produce an ordered list of elements corresponding to region R, thereby producing a plurality of ordered lists of elements corresponding to the plurality of regions; and
- (H) combining the plurality of ordered lists of elements, in decreasing order of the weight sums corresponding to the plurality of ordered lists, to produce an ordered list of the plurality of elements.

10. The method of claim 9, wherein a particular one of the regions corresponds to a combination of the first and second attributes, and wherein (G) comprises assigning an order to elements having the first attribute in the particular one of the regions based on an order of elements having the second attribute in the particular one of the regions.

11. A non-transitory computer-readable medium having computer-readable instructions tangibly stored thereon, wherein the computer-readable instructions are executable by a computer processor to perform a method for ordering a plurality of elements, wherein each of the plurality of elements has at least one corresponding attribute, the method comprising:
- (A) identifying a first subset of the plurality of elements associated with a first attribute by selecting, from among the plurality of elements, at least one element having the first attribute;
- (B) identifying a first weight associated with the first attribute;
- (C) identifying a second subset of the plurality of elements associated with a second attribute by selecting, from among the plurality of elements, at least one element having the second attribute;
- (D) identifying a second weight associated with the second attribute, wherein the second weight differs from the first weight;
- (E) identifying a plurality of regions, each of which corresponds to a distinct combination of zero or more of the first and second attributes, wherein the plurality of regions includes a first region including a first and second element in the plurality of elements and a second region including a third and fourth element in the plurality of elements;
- (F) for each region R in the plurality of regions, identifying a corresponding weight sum for region R comprising a sum of the weights of the zero or more attributes corresponding to R;
- (G) for each region R, ordering elements within region R to produce an ordered list of elements corresponding to region R, thereby producing a plurality of ordered lists of elements corresponding to the plurality of regions; and
- (H) combining the plurality of ordered lists of elements, in decreasing order of the weight sums corresponding to the plurality of ordered lists, to produce an ordered list of the plurality of elements.

12. The non-transitory computer-readable medium of claim 11, wherein a particular one of the regions corresponds to a combination of the first and second attributes, and wherein (G) comprises assigning an order to elements having the first attribute in the particular one of the regions based on an order of elements having the second attribute in the particular one of the regions.

* * * * *

UNITED STATES PATENT AND TRADEMARK OFFICE
CERTIFICATE OF CORRECTION

PATENT NO. : 8,407,234 B1
APPLICATION NO. : 12/758074
DATED : March 26, 2013
INVENTOR(S) : Thomas Justin Buschbach Page 1 of 1

It is certified that error appears in the above-identified patent and that said Letters Patent is hereby corrected as shown below:

On title page, item (56), under "OTHER PUBLICATIONS", in column 2, line 3, Delete "Processing" and insert -- Proceedings --, thereof.

In the Specifications:

In column 3, line 66, Delete "possesed" and insert -- possessed --, thereof.

In column 9, line 50, Delete "orderer" and insert -- sorter --, thereof.

Signed and Sealed this
Twenty-seventh Day of August, 2013

Teresa Stanek Rea
*Acting Director of the United States Patent and Trademark Office*